United States Patent
Schulte et al.

(10) Patent No.: US 11,819,681 B2
(45) Date of Patent: Nov. 21, 2023

(54) IMPLANTABLE ELECTRODE ARRANGEMENT AND METHOD OF MANUFACTURE

(71) Applicant: Albert-Ludwigs-Universität Freiburg, Freiburg (DE)

(72) Inventors: Jennifer Schulte, Freiburg (DE); Thomas Stieglitz, Freiburg (DE); Max Eickenscheidt, Freiburg (DE)

(73) Assignee: Albert-Ludwigs-Universität Freiburg, Freiburg (DE)

( * ) Notice: Subject to any disclaimer, the term of this patent is extended or adjusted under 35 U.S.C. 154(b) by 324 days.

(21) Appl. No.: 17/067,005

(22) Filed: Oct. 9, 2020

(65) Prior Publication Data

US 2021/0106814 A1 Apr. 15, 2021

(30) Foreign Application Priority Data

Oct. 11, 2019 (DE) ...................... 10 2019 215 673.8

(51) Int. Cl.
*A61N 1/05* (2006.01)
(52) U.S. Cl.
CPC .......... *A61N 1/05* (2013.01); *A61B 2562/125* (2013.01)
(58) Field of Classification Search
CPC ... A61N 1/05; A61N 1/37; A61N 1/44; A61B 2562/125
See application file for complete search history.

(56) References Cited

U.S. PATENT DOCUMENTS

| 5,571,158 A | 11/1996 | Bolz et al. |
| 2015/0148879 A1 | 5/2015 | Rump et al. |
| 2019/0030318 A1 | 1/2019 | Lee et al. |

FOREIGN PATENT DOCUMENTS

| DE | 4207368 A1 | 2/1993 |
| DE | 19927615 A1 | 1/2001 |
| EP | 0597995 B1 | 8/1992 |

OTHER PUBLICATIONS

European Patent Office communication, dated Feb. 15, 2021, 7 pages.
German Office Action, dated Jul. 2, 2020, 6 pages.

*Primary Examiner* — Mark W. Bockelman
(74) *Attorney, Agent, or Firm* — Barley Snyder

(57) ABSTRACT

An implantable electrode arrangement includes an electrically insulating carrier structure and an electrically conductive layer including an electrically conductive thin film layer. The electrically conductive thin film layer is structured to form at least one implantable electrode. The at least one implantable electrode has a local fractalization through a self-similar structuring chosen such that a mechanical resonance of the electrode in response to electric excitation with an excitation voltage is minimized.

16 Claims, 13 Drawing Sheets

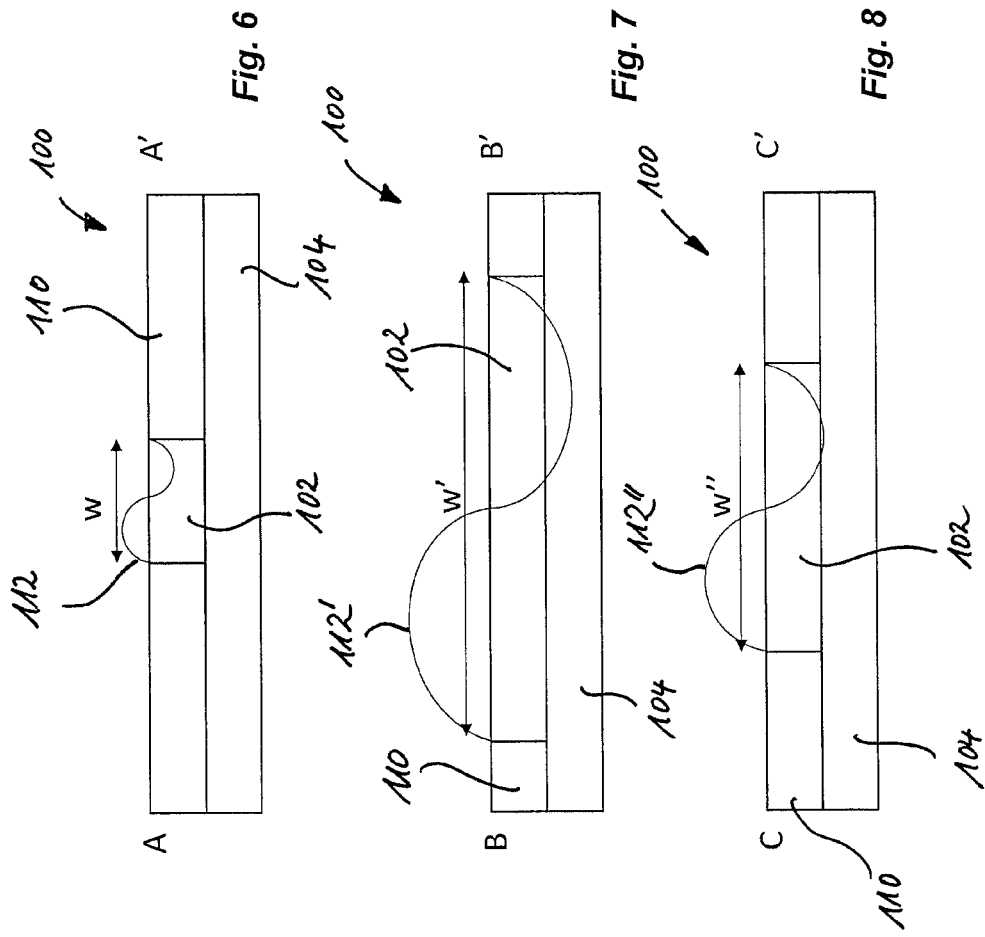
Fig. 6
Fig. 7
Fig. 8
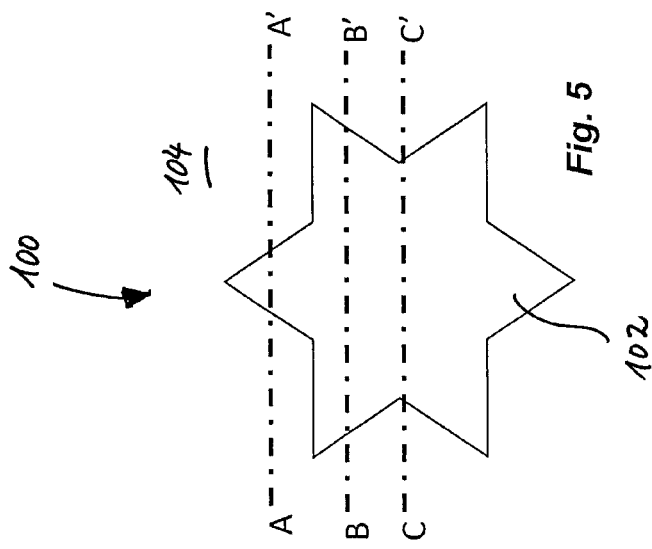
Fig. 5

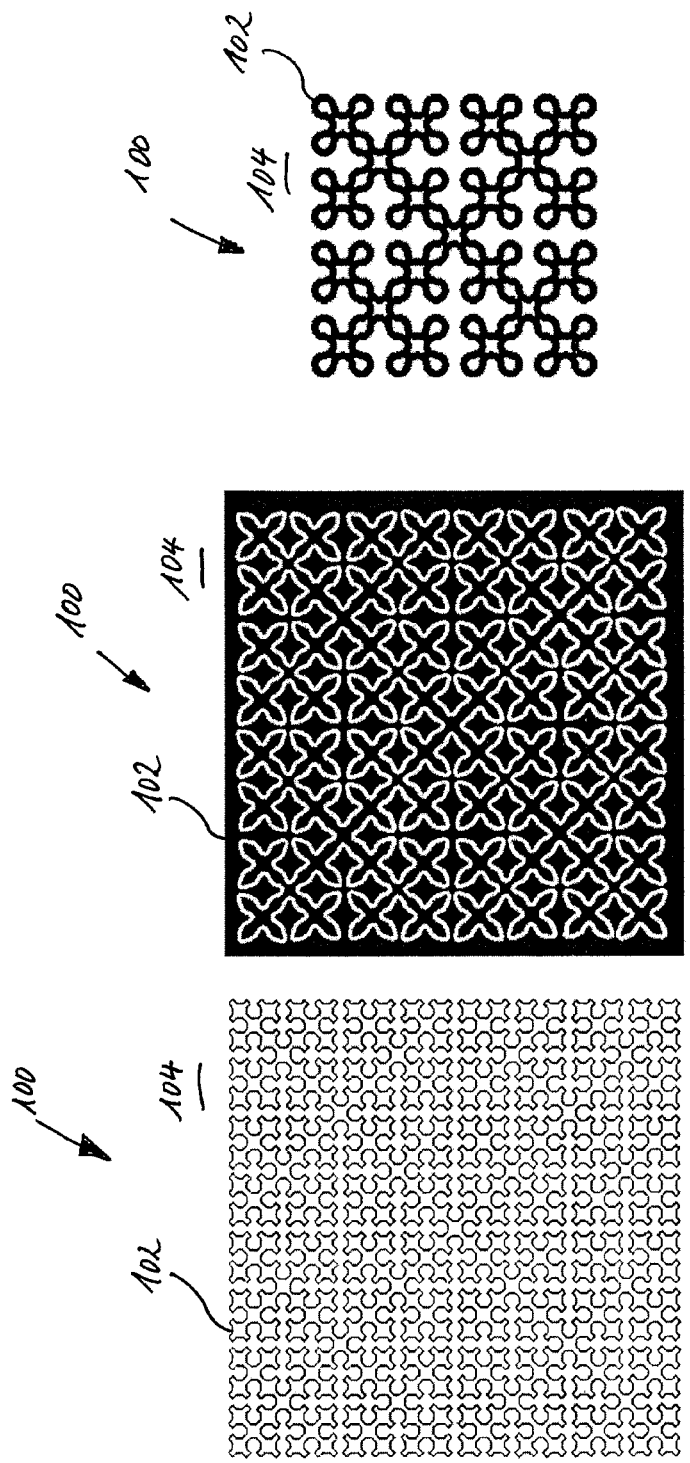

IMPLANTABLE ELECTRODE ARRANGEMENT AND METHOD OF MANUFACTURE

CROSS-REFERENCE TO RELATED APPLICATION

This application claims the benefit of the filing date under 35 U.S.C. § 119(a)-(d) of German Patent Application No. 102019215673.8, filed on Oct. 11, 2019.

FIELD OF THE INVENTION

The present invention relates to flexible implantable electrode arrangements, e.g. electrode arrays, and to an associated design method. In particular, the present invention deals with the design of electrode arrangements with a thin film metallization.

BACKGROUND

Recent research and development in the field of neural engineering have led to a large number of active implantable medical devices (AIMD), which can be used in a wide range of applications. These devices usually consist of a housing comprising control electronics and a battery, implantable electrodes (or electrode arrays) and cables for electrically contacting the electrodes and electronics. The electrodes are used for electrically stimulating cells or for recording physiological signals.

Neuronal electrodes thus serve as an interface between the biological and the technical system, their main function being the recording and/or excitation of neuronal signals. When neural electrodes are used in AIMDs, they play a key role in restoring and maintaining body functions of patients with physical handicaps and also psychiatric disorders. Such electrodes have an electrically conductive material for the contact areas and the connection points as well as a substrate material that insulates the electrically conductive materials. Essential prerequisites for the success of implantable medical devices are an advantageous tissue/electrode interaction on the one hand and sufficient biostability on the other. For this reason, the mechanical flexibility of the electrode is an essential aspect in the design of neuronal probes in order to achieve a structural biocompatibility, and to thus reduce the foreign body reaction and increase the service life of the implant.

In particular, implantable systems are used, which make use of electrode metallizations based on thin film technology so as to support or restore failing body functions and sensory functions through targeted, specific electrical interaction with individual neurons in the nervous system, and so as to correct organ dysfunctions. In order to achieve the high spatial resolution required for this purpose, the electrode metallizations are realized as thin layers on a carrier substrate with diameters in the micrometer range and layer thicknesses of only a few hundred nanometers. Miniaturization leads to a loss of the chemical, physical and mechanical stability of the metals in case of delamination and thus to a premature functional failure, since the thin films have thicknesses in the range of or below individual grains in the microstructure.

Existing electrodes based on thin film technology suffer from degradation mechanisms, such as corrosion, crack formation and loss of adhesion and, consequently, delamination of the thin film from the carrier substrate as a result of chemical and physical material fatigue and release of strain energy.

Most conventional thin film electrodes use platinum as a metallization layer applied by thin film techniques or platinum with an iridium/iridium oxide film sputtered onto the platinum with or without adhesion promoting layers to the carrier substrate.

The cyclically alternating oxidation and reduction reactions of the metallization surface in case of electrical stimulation lead to alternating chemical material changes caused by oxidation, chloride complex formation, hydrogen embrittlement or volume expansion due to hydrogen intercalation and resultant propagation of mechanical stresses (tensile and compressive stresses) in the microstructure, whereby fatigue and deformation processes, such as plastic deformation, crack formation and loss of adhesion of the thin films and interfaces, are caused.

Due to the reaction rates during electrical stimulation, which are usually not chemically balanced, and the corrosion aggravated by the flow of electric current, deformation mechanisms will occur more quickly.

For example, the article by J. Pfau, T. Stieglitz, and J. Ordonez, "Mechanical deformation and chemical degradation of thin-film platinum under aging and electrical stimulation," in 2017 *8th International IEEE/EMBS Conference on Neural Engineering (NER)*: 25-28 May 2017, Shanghai, China, 2017, pp. 166-169, deals with aging and degradation processes of implantable electrodes. The document describes the influence of electrical stimulation on electrode aging. The cause of deformation is in particular seen in the alternating incorporation and expulsion of oxygen and hydrogen. In addition, the article by J. S. Ordonez, L. Rudmann, P. Cvancara, C. Bentler, and T. Stieglitz, "Mechanical deformation of thin film platinum under electrical stimulation", Conference proceedings: *Annual International Conference of the IEEE Engineering in Medicine and Biology Society. IEEE Engineering in Medicine and Biology Society. Annual Conference*, vol. 2015, pp. 1045-1048, 2015, describes the occurrence of mechanical deformation due to electrical stimulation of platinum thin film electrodes.

In order to guarantee the functionality of the electrodes over the entire period of intervention with the nervous system, it will be necessary to compensate or, if possible, eliminate the defect mechanisms occurring. Therefore, there is a need for a method to design flexible implantable electrode arrangements that overcomes the drawbacks of the known solutions, so that the manufactured electrode arrangements will be safe and reliable, but still can be produced in a cost-effective manner and on the basis of standard technology. Furthermore, there is a need for such a flexible implantable electrode arrangement.

SUMMARY

An implantable electrode arrangement includes an electrically insulating carrier structure and an electrically conductive layer including an electrically conductive thin film layer. The electrically conductive thin film layer is structured to form at least one implantable electrode. The at least one implantable electrode has a local fractalization through a self-similar structuring chosen such that a mechanical resonance of the electrode in response to electric excitation with an excitation voltage is minimized.

BRIEF DESCRIPTION OF THE DRAWINGS

Further features and advantages will become apparent from the following and more detailed description of the invention, as illustrated in the accompanying drawings, in which:

FIG. 5 is a schematic top view of an electrode arrangement according to another embodiment;

FIG. 6 is a sectional side view taken along line A-A' of FIG. 5;

FIG. 7 is a sectional side view taken along line B-B' of FIG. 5;

FIG. 8 is a sectional side view taken along line C-C' of FIG. 5;

FIG. 19 is a schematic top view of an electrode arrangement according to another embodiment;

FIG. 20 is a schematic top view of an electrode arrangement according to another embodiment;

FIG. 21 is a schematic top view of an electrode arrangement according to another embodiment;

DETAILED DESCRIPTION OF THE EMBODIMENT(S)

Figure 2:
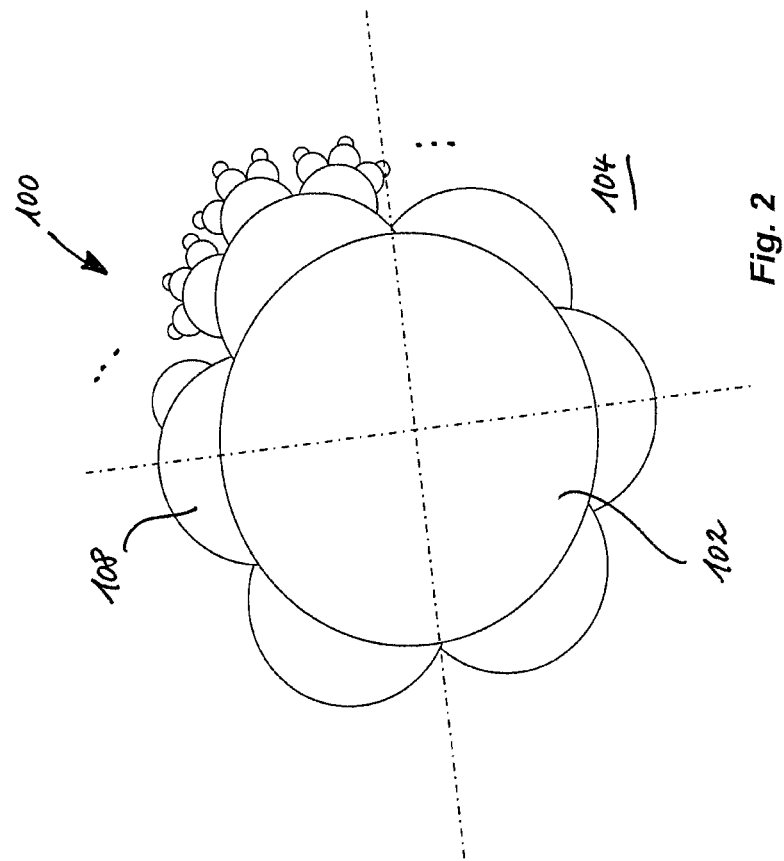
FIG. 2 is a schematic top view of an electrode arrangement according to another embodiment.

For making the present invention more easily understandable, it will be explained in more detail hereinafter on the basis of the embodiments shown in the figures. In so doing, like components will be provided with like reference numerals and like component designations. In addition, some features or combinations of features of the depicted and described different embodiments may also separately represent independent, inventive solutions or solutions according to the present invention.

The present invention is based on the idea of designing electrodes in accordance with their mechanical oscillation response to the electric field parameters acting thereon for stimulation under the aspect of accomplishing an oscillation compensation adapted to the stimulation parameters, and a deformation minimum. Up to now, electrodes have never been regarded as an electrically stimulated system that is capable of oscillating (oscillator) and have therefore never been investigated with respect to a mechanical oscillation response to electrochemical stimulation. As a result, former electrode design approaches completely disregarded the electrochemical/mechanical stress coupling and, due to a lack of stress compensation, had a chemical and mechanical stability that did not suffice for chronic implantation and electrical stimulation.

The inventors of the present invention realized that an optimization of the electrodes with respect to the lowest possible resonance in response to excitation voltages with frequencies (in the range of 1 Hz-100 kHz, between 1 Hz and 10 kHz and between 20 kHz and 40 kHz) and pulse shapes important for the electric stimulation of nerves has the effect that the above described failure and degradation mechanisms do not occur at all or only in a moderated form.

The thin film electrodes according to the embodiments described below are designed, by locally changing and adapting the geometric shape and the structuring of the surface topography and of the adhesion promoting layer topography, for a global oscillation minimum for the frequencies in the range of 1 Hz-100 kHz and the pulse shapes that are important for electrically stimulating nerves. The design approaches are adapted in such a way that the mechanical oscillation is locally adapted by local mechanical strengthening or weakening of the electrode structure and/or topography so as to reduce the global mechanical resonance (in oscillation amplitude and natural oscillation frequency behavior) of the electrode.

In an embodiment, an outer electrode cutout, which is exposed through the carrier substrate, is chosen as a boundary condition such that it occupies the same global area of the electrode on the carrier substrate as a standard electrode with a circular opening. The design structuring is chosen such that the mechanical oscillation and the resonance in response to the applied electric field will be reduced. The changes in the electrode design relate to local (not global) adaptations of the geometry and topography of the electrode. In an embodiment, thin films with layer thicknesses in the range of 10 nm up to 2 μm are taken as a basis. An associated adhesion promoting layer has a thickness in the range between 10 nm and 50 nm.

An implantable electrode arrangement comprises an electrically insulating carrier structure and an electrically conductive layer including an electrically conductive thin film layer, the electrically conductive thin film layer being structured so as to form at least one implantable electrode. According to the present invention, the at least one electrode exhibits a local self-similarity (fractalization), which is chosen such that a mechanical resonance of the electrode in response to electric excitation with an excitation signal, in particular an excitation voltage or an excitation current, will assume a minimum. In particular, the electrode exhibits a self-similarity of the edge area or the base area or of the topography. The geometry may here have a fractal dimension, i.e. a dimension of a non-integer real number. For example, the electrode may comprise a spiral line resulting in a circular area. The desired resonance behavior is accomplished by the geometrical shape of the electrode.

The electric field distribution is optimized to the desired mechanical oscillation deformation of the thin film electrode. In so doing, the electric field distribution occurring and thus the associated mechanical oscillation are changed locally. In this way, a global minimization of oscillations is achieved. This can be accomplished, for example, by different approaches to the self-similarity of the edge area, the local thin film geometry, the thin film topography, the adhesion promoter topography between the thin film and the carrier substrate and by damping achieved by self-similar structures on the substrate, which rests on the thin film surface, as described below. For all the approaches, thin films are taken as a basis, the global electrode geometry and the electrode cutouts in the substrate remaining unchanged in comparison with known arrangements in order to fit the dimensions of conventionally used thin film electrodes.

The following terms and definitions will be used hereinafter:

The term "fractal" was coined by Benoit B. Mandelbrot and is derived from the Latin term "frangere", which means broken, fragmented or uneven. The term fractal is derived from a characteristic of the forms referred to, namely from the number which, in contrast to the topological dimension, is a fractional number describing the relationship between linear expansion and surface area (or volume) of a form. The most important characteristics of a fractal are its fractal dimension (in the following also referred to as fractality factor) and the so-called self-similarity. Due to the broken edge of a fractal, an integer dimension, such as a straight line with the dimension 1, a rectangle with the dimension 2 or a 3-dimensional cube, cannot be associated therewith. Rather, the dimensions of a fractal lie between the integers. Fractal shapes are also self-similar, i.e. the overall structure of a fractal is composed of smaller structures having the same shape as the overall structure. A figure is described as being self-similar, if parts of the figure are small copies of the whole figure. A figure is exactly self-similar, if it can be broken down into parts that are exact copies of the whole figure. Any part contains an exact copy of the whole figure.

The term "fractalization" comprises any kind of discontinuity in the area or in the three-dimensional structure of an electrode, which influences the resonance behavior of the electrode. "Fractalization" is intended to mean that the structure of the electrode is, at least in certain areas thereof, interrupted by discontinuities as regards its contour, its thickness, its connection to the subsurface or its surface. These discontinuities have the effect that the mechanical resonance behavior of the electrode in response to excitation by an alternating voltage or an electric pulse sequence will change.

The term "thin film electrode" refers to an electrically conductive layer with layer thicknesses in a range between 10 nm and 5 µm, or between 50 nm and 2 µm in an embodiment. As regards the film forming process in the production of such thin film electrodes, a physical or chemical process is used. The physical processes are known as physical deposition (PVD) and comprise vacuum deposition processes, a molecular beam epitaxy process, a sputtering process, an ionization vapor deposition process and a laser abrasion process. The chemical processes are known as chemical vapor deposition (CVD) and comprise thermal CVD, plasma CVD and MOCVD (metal organic chemical vapor deposition), etc. Among these processes, the sputtering process is particularly effective.

In the context of the present invention, the term "flexible" means that a layer or a substrate is bendable and in particular deformable within certain limits, without breaking or, at any rate, without losing the desired electrical and mechanical characteristics.

The term "electrically conductive" means hereinafter that a material is capable of conducting electric current and is suitable for forming electrodes. In addition to the conductivity exhibited e.g. by metals, the term "electrically conductive" shall, within the meaning of the present invention, also include the conductivity of a semiconducting material.

In the following, the present invention will be explained in more detail with reference to the figures, and first, in particular, with reference to the schematic view according to FIG. 1. Reference is made to the fact that the size ratios and in particular the layer thickness proportions are not necessarily reproduced true to scale in all the figures. Also, the degree of fractalization is in most cases not shown with the actual depth and structural fineness so as not to impair the clarity.

Figure 1:
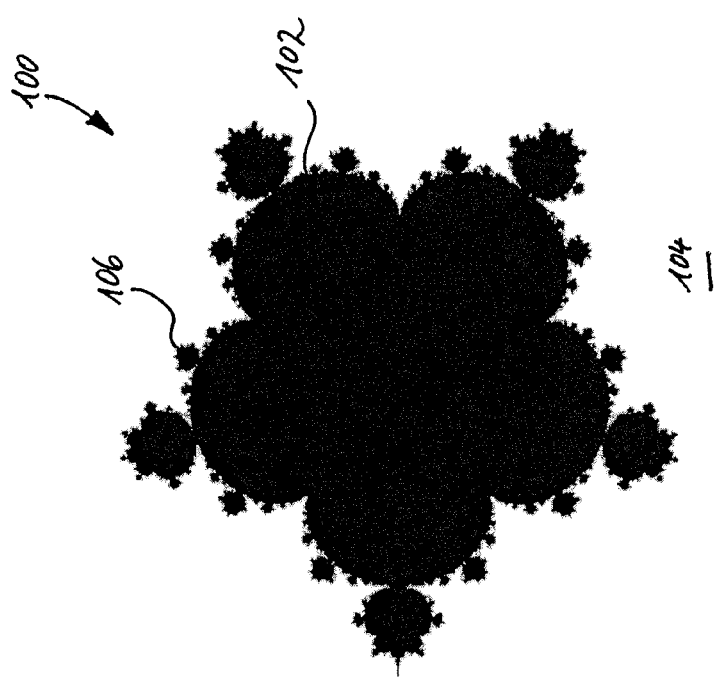
FIG. 1 is a schematic top view of an electrode arrangement according to an embodiment.

FIG. 1 shows in a top view an exemplary embodiment of an electrode arrangement 100 according to a first embodiment of the present invention. In an embodiment, the electrode arrangement 100 is an implantable electrode arrangement. The electrode arrangement 100 comprises as an electrically conductive layer a thin film metallization 102, which is deposited on a carrier structure 104. The carrier structure 104 is electrically insulating. The thin film metallization 102 consists e.g. of sputtered platinum and the carrier structure 104 comprises a flexible polymer, e.g. polyimide. A person skilled in the art will, of course, be aware that also other electrically conductive materials may be used as an electrically conductive layer and that the carrier structure 104 may be produced from any electrically conductive material.

The thin film metallization 102 is structured such that mechanical oscillation in response to an applied field will be reduced, by fractalizing an edge 106 by repeating self-similar elements that become smaller and smaller in the form of a fractal Mandelbrot structure. The self-similarity is of the edge 106 or a base area or of the topography of the thin film metallization 102. The geometry may here have a fractal dimension, i.e. a dimension of a non-integer real number. For example, the electrode may comprise a spiral line resulting in a circular area.

Due to this discontinuity of a smooth continuous contour shape of the electrode, it can be achieved that when an electric field is applied, e.g. a sinusoidal alternating field or a voltage pulse sequence, the thin-film metallization 102 will not be set into resonant oscillations and will thus not be deflected to such an extent that delamination occurs. The degree of fractalization, i.e. the number of self-similar elements that are joined to one another, depends, of course, on the structural accuracies that can be achieved and usually ends at the fourth or fifth stage.

The fractalized embodiment contour shown in FIG. 1 is chosen such that the largest diameter occurring will be compatible with standard electrode areas, so that no change in technology will be necessary when the electrode is exposed by removing a top layer.

For the polymer material of the carrier structure 104, a great variety of plastic materials may be used. The polymer material includes, for example, polyimide, PI, polyethylene terephthalate, PET, polyethylene, PE, polycabonate, PC, polyvinyl chloride, PVC, polyamide, PA, polytetrafluoroethylene, PTFE, polymethyl methacrylate, PMMA, polyetheretherketone, PEEK, polysulfone, PSU, polyp-xylylene), polydimethylsiloxane, PDMS, and/or polypropylene, PP. The carrier structure 104 and an additional top layer may be made of the same material or of different materials. Polyimide has several advantages: on the one hand, it is particularly inert and chemically stable in a fully cross-linked state. On the other hand, it can be applied by spinning on in the form of a liquid precursor and it also has a second, solid but not yet completely cured preform, in the case of which subsequent layers will adhere more easily, by way of example. Finally, there are photo-structurable polyimide resin systems, which allow the contact pads to be opened easily, e.g. for producing a top layer.

The thin film layer 102 of the electrode arrangement 100 may comprise a metallization consisting of e.g. platinum, iridium, platinum-iridium and/or iridium oxide, but also tantalum, gold or any other electrically conductive material. Platinum has the advantage of a very high chemical long-term stability. Furthermore, the thin film metal layers may be coated with other metals, such as rough platinum, iridium oxide, but also with carbonic materials (e.g. graphene, glassy carbon, laser-induced carbon).

FIG. 2 schematically illustrates the structure of an electrode arrangement 100 similar to that of FIG. 1, this illustration showing only part of the electrode edge 106 such that the latter comprises crescent-shaped extensions 108 down to the fourth reduction stage. The electrode arrangement 100 is, in reality, provided with the crescent-shaped extensions all around. The reduction stage may here go as far as necessary for achieving the desired aim and as far as possible from the point of view of the manufacturable structural dimensions. In FIG. 2, the circular structure has attached thereto six crescent-shaped extensions 108, which each carry three extensions. The electrode arrangement according to FIG. 1, however, has a fivefold structure. A person skilled in the art will, however, be aware that also other numbers of extensions 108 may be chosen. This discontinuous structural design of the electrode contour reduces the resonance ability of the thin film metallization 102 in the event of excitation with an excitation signal, such as a voltage pulse sequence or a current pulse sequence with frequencies between 1 kHz and 10 kHz, so that the detachment effects occurring with known electrode arrangements can be prevented.

Figure 3:
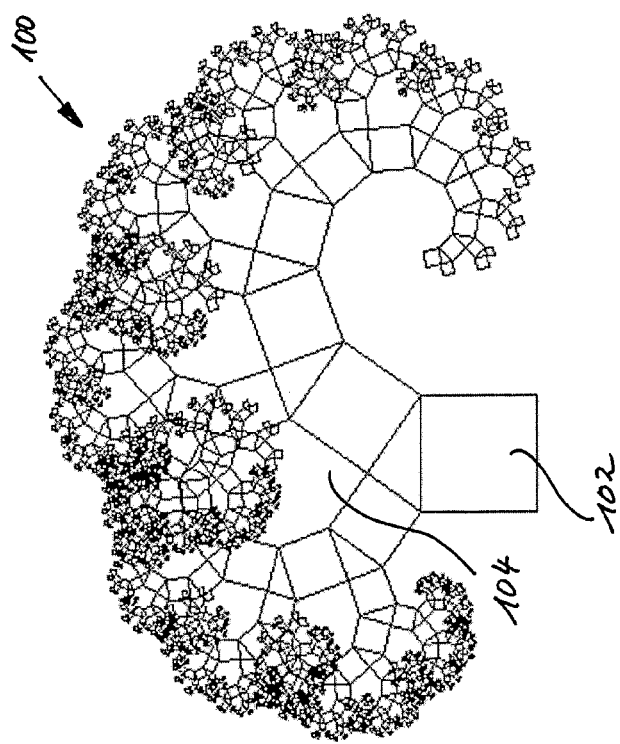
FIG. 3 is a schematic top view of an electrode arrangement according to another embodiment.

As shown in FIG. 3, a fractal based on the Pythagoras tree is also suitable for generating a fractalization of the electrode edge, this fractal being shown in FIG. 3. A starting point is the lower right-angled triangle. The squares above the hypotenuse and the cathetuses are drawn on this triangle. A further triangle similar to the first triangle is constructed on each of the cathetus squares. The cathetuses of these triangles have again squares added thereto—step 2 is reached. According to this method, the procedure is continued step by step. Instead of a square, other shapes, e.g. regular hexagons, may be added as well.

In an embodiment, the local fractalization includes a structuring of the contour of the electrode, so that locally different conditions between an electrode diameter and the electrode area are set. For example, the electrode contour may have a star-shaped self-similar geometry, comparable to the fractal object of a Koch curve. Examples relevant to the electrode structure according to the present invention are fractal line objects which, due to their self-similarity, lead to an area-filling object (area object), in particular fractals of the Koch curve, Hilbert curve, Gosper curve, Levy C curve, Peano curve etc. In addition, the local fractalization may also include an interruption of the electrically conductive layer which is effective towards the outside.

Figure 4:
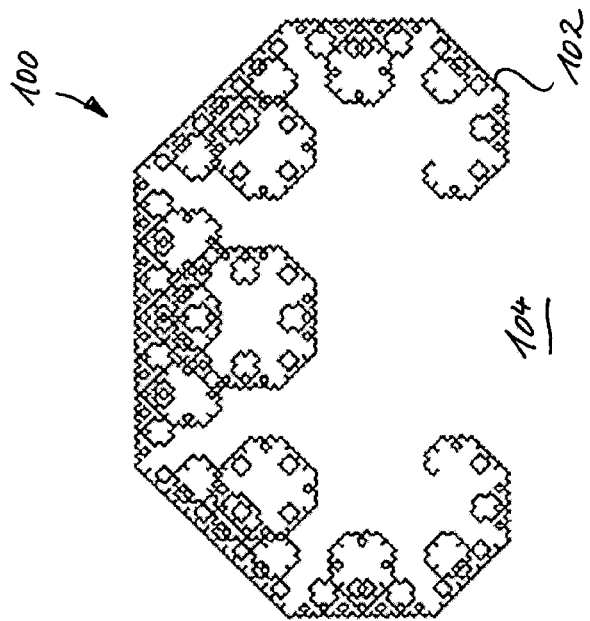
FIG. 4 is a schematic top view of an electrode arrangement according to another embodiment.

A possibility of fractalizing the electrode edge is the use of a Levy C curve, which is shown in FIG. 4.

Furthermore, also the local diameter may be varied. Contour designs of an electrode arrangement 100 based on the so-called Koch star or Koch snowflake are illustrated in FIGS. 5 to 11.

Figure 11:
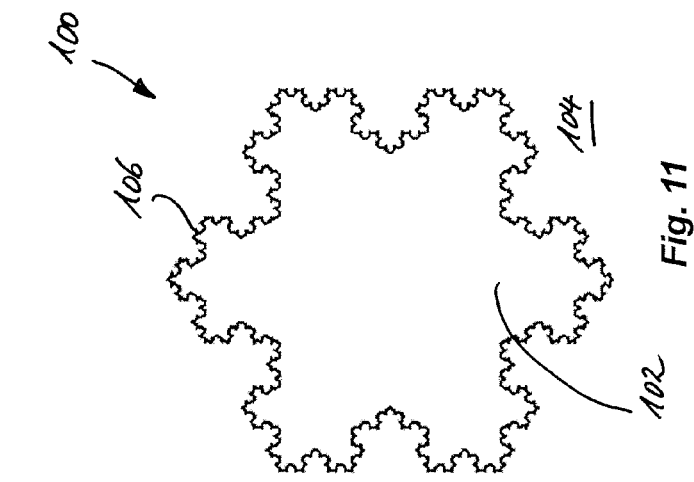
FIG. 11 is a schematic top view of an electrode arrangement according to another embodiment.
Figure 10:
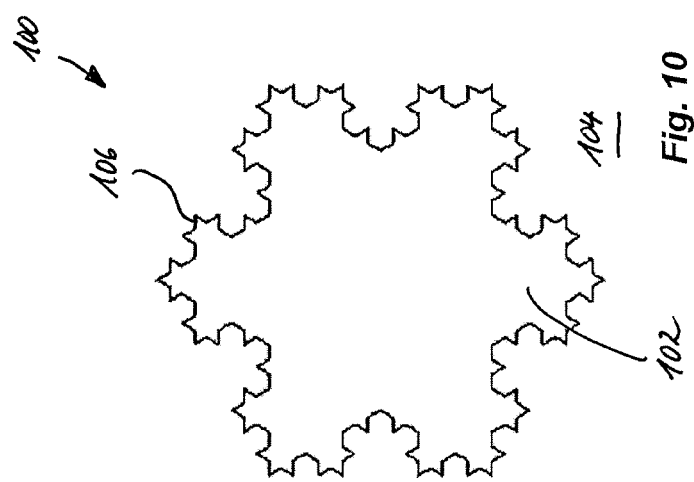
FIG. 10 is a schematic top view of an electrode arrangement according to another embodiment.
Figure 9:
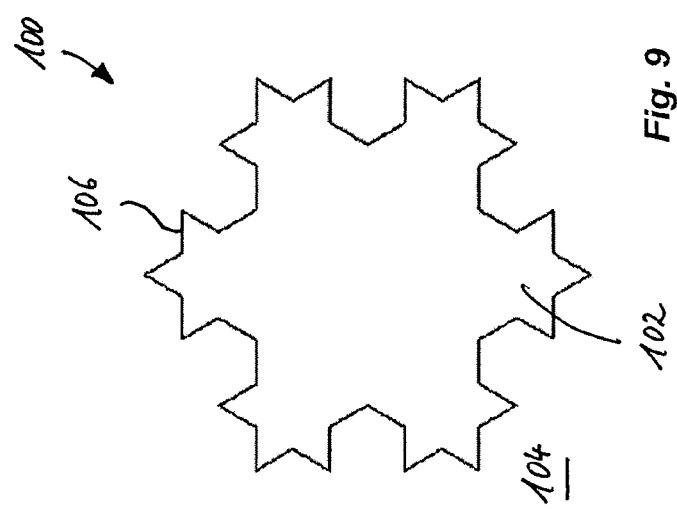
FIG. 9 is a schematic top view of an electrode arrangement according to another embodiment.

As first shown in FIG. 5, the electrically conductive layer 102 has a star-shaped contour. The so-called Koch curve (also referred to as snowflake curve) is, in its simplest form, an equilateral triangle. Each side is divided into three and the middle section has added thereto an equilateral triangle towards the outside. In the following steps, each straight piece can be dealt with analogously, as can be seen in FIGS. 9 to 11. FIG. 5 shows the first fractalization step with a six-pointed star.

FIGS. 6, 7 and 8 show sections along the section lines A-A', B-B' and C-C'. From these sectional views it can be seen that the electrically conductive structure 102 is embedded in a top layer 110. The top layer 110, in an embodiment, consists of the same material as the carrier structure 104, which is also referred to as substrate. According to the present invention, the wavelengths of the possible resonant oscillations differ from each other due to the different local diameters w, w' and w". The oscillation curves 112, 112' and 112" are plotted schematically for the respective diameters w, w' and w". Hence, the ratio of the electrode diameter to the total area as well as to the cross-sectional area differs locally and a global resonance of the thin film metallization 102 is prevented.

FIGS. 9 to 11 illustrate further stages of Koch's snowflake with ever finer splitting up of the electrode edge 106 by applying the above mathematical instruction. A person skilled in the art will be aware that any fractalization stages can be used, depending on the accomplishable structural fineness and the resultant effect of resonance reduction. In general, also other contour fractalizations (not shown here), such as Kepler's fractals, may be used.

In particular, a local area-to-edge ratio may be kept constant throughout the electrode according to the present invention, so that an edge effect will also be created at the center of the electrode. This is accomplished, for example, by filling a given electrode contour with line structures, such as spirals and/or a Hilbert or Gosper curve. This creates throughout the electrode, and even at the center thereof, a uniform edge effect of the electric field applied to the electrode cutout. In particular, the local dimensions/relationships of substrate opening to substrate are chosen such that a local microelectrode effect with superimposed electric fields and thus superimposed ion currents is created. These local electric field components are intended to superimpose one another such that they form again a global homogeneous electric field with respect to the electrode cutout in the substrate (what is here meant is the outer diameter/opening/basic geometry of the electrode). The fractalization of the electrode area achieves the local change of the mechanical oscillation characteristics, with the global effective radius of the electrode remaining the same, so as to adapt the local mechanical oscillation and minimize the global resonance. In other words, the geometric area is adapted such that the desired resonance behavior is achieved.

A further optimization is achieved due to the increase in the circumference-to-area ratio by fractalizing the edge and by the resultant increase in electrode circumference, without any change of electrode area.

Figure 12:
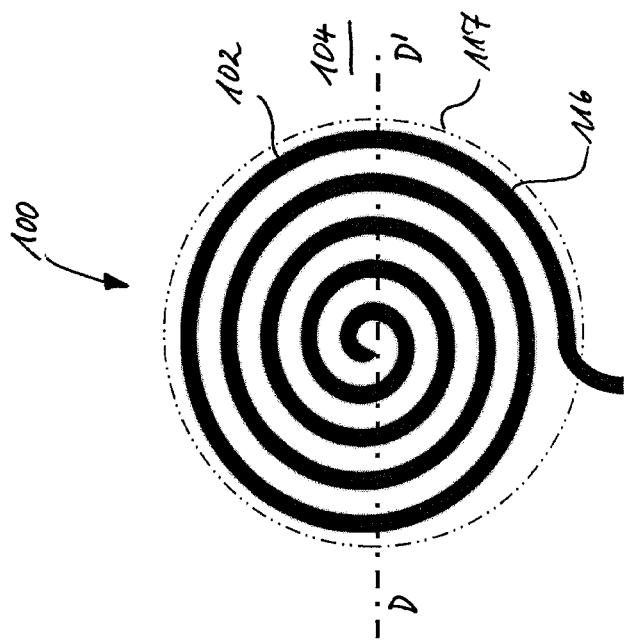
FIG. 12 is a schematic top view of an electrode arrangement according to another embodiment.

According to a further embodiment, which will be explained hereinafter with reference to FIGS. 12 to 23, the electrode area may also be strip-shaped and it may be interrupted by an electrically insulating material. This modifies the geometric area of the thin film metallization such that the mechanical resonance will be minimal when an excitation voltage is applied. In the case of this embodiment, the ratio between the local electrode diameter w and the total area (as well as the cross-sectional area) remains constant over the entire electrode arrangement 100. For example, the electrode area 102 may be formed by a spiral-shaped conductive strip 116, as illustrated in FIG. 12. As indicated by the dot-and-dash circular line 117, the conductor path spiral is formed within an opening in the insulating top layer. This means that the active electrode area could, for example, correspond to the usual diameters and that no adaptation will be required as regards the devices that work with the thin film electrode. One end of the conductor path spiral is configured as an electrical connection for feeding the electrical signal, while the other end remains open.

Figure 13:
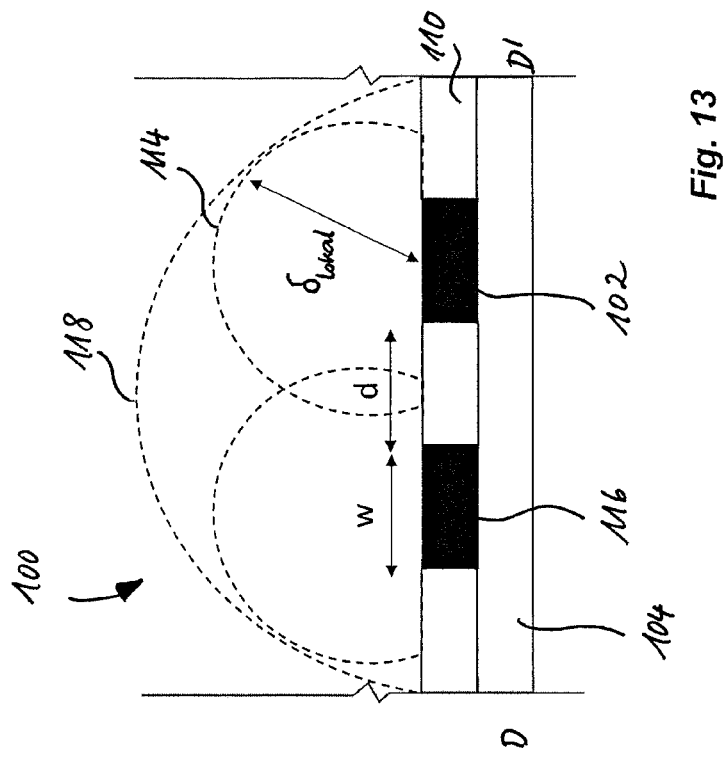
FIG. 13 is a sectional side view of FIG. 12.

FIG. 13 illustrates, as a detail of the cross-section through the top view according to FIG. 12, the electric fields occurring. Each strip-shaped part 116 of the electrically conductive layer 102 is surrounded by an electric field 114 which leads to a local ion current $\delta_{lokal}$. The conductor path width w and the distances d between the conductive parts are expediently chosen such that the local ion currents $\delta_{lokal}$ and the local electric fields add up to a homogeneous global electric field 118. In other words, a local microelectrode effect with superimposed electric fields 114 and thus superimposed ion currents $\delta_{lokal}$ is produced, and these local electric field components 114 are intended to superimpose one another, so as to form again a global homogeneous electric field 118 with respect to the electrode cutout 117 in the substrate (what is here meant is the outer diameter/opening/basic geometry of the electrode). The fractalization of the electrode area achieves the local change of the mechanical oscillation characteristics, with the global effective radius of the electrode remaining the same, so as to adapt the local mechanical oscillation and minimize the global resonance.

The spiral structure shown in FIG. 12 is only one of many possibilities of interrupting the thin film metallization 102 in a defined way. The interruption may be formed by partially covering the electrically conductive layer with an electrically insulating layer or by embedding electrically conductive paths into the electrically insulating carrier structure. In the first case, local mechanical oscillation damping can be achieved from the upper side, while in the second case the local ion currents are influenced directly.

Figure 14:
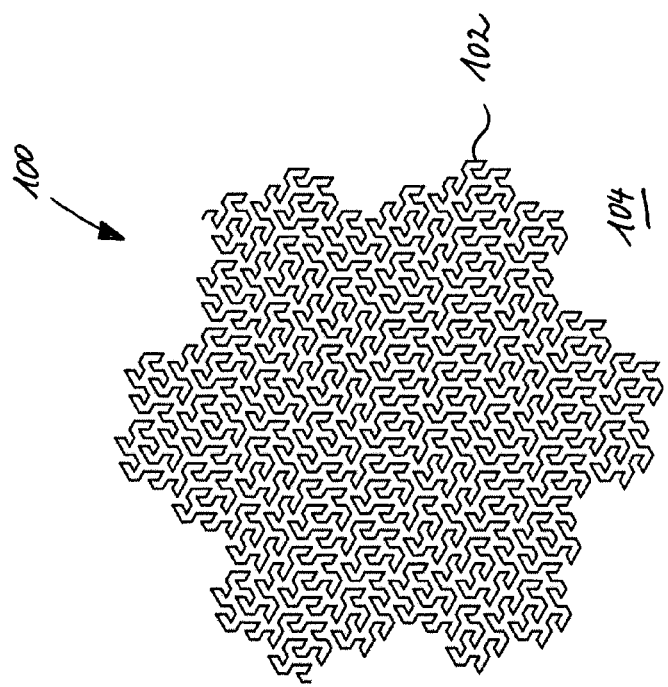
FIG. 14 is a schematic top view of an electrode arrangement according to another embodiment.

As shown in FIG. 14, the conductor path 116 may have the shape of a so-called Gosper curve. The Gosper curve is a fractal object created by replacing line segments. For example, the curve shown in FIG. 14 is a fourth-stage Gosper curve. Other stages may, of course, be used as well. Alternatively, the Gosper curve may also define the position of the insulating areas 104 and the areas that are white in FIG. 14 are electrically conductive.

Figure 15:
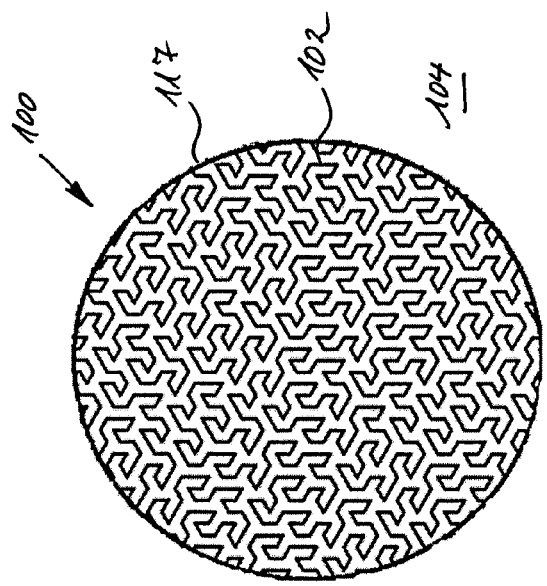
FIG. 15 is a schematic top view of an electrode arrangement according to another embodiment.

As shown in FIG. 15, the fractalized electrode area may also have a peripheral shape that is not determined by the fractal curve. This may be a circular boundary, by way of example. Other shapes of the outer boundary 117, such as a polygonal outline, are of course possible as well.

Figure 18:
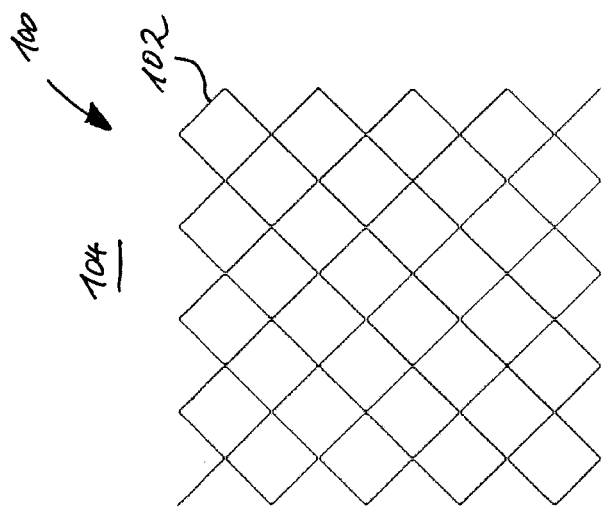
FIG. 18 is a schematic top view of an electrode arrangement according to another embodiment.
Figure 17:
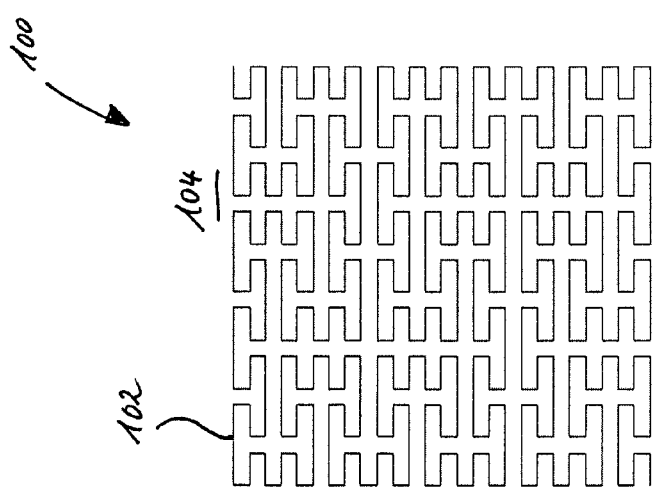
FIG. 17 is a schematic top view of an electrode arrangement according to another embodiment.
Figure 16:
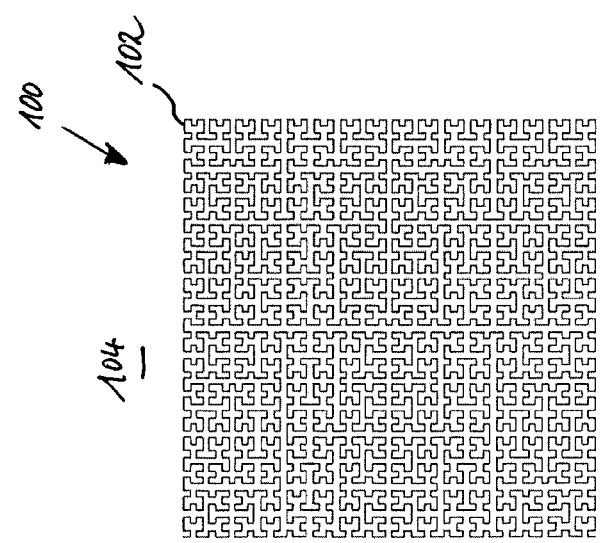
FIG. 16 is a schematic top view of an electrode arrangement according to another embodiment.

FIGS. 16 to 18 illustrate further examples of areally fractalized thin film metallizations 102. For example, FIG. 16 shows a Hilbert fractalization and FIG. 17 a Peano fractalization. The Peano curve is a self-similar plane-filling curve with the fractal dimension 2. FIG. 18 shows another example of a Peano curve, referred to as 1:⅓ fractalization. Although FIGS. 16 to 18 schematically show a rectangular outer contour of the electrode, the thin film metallization 102 may have any outer contour, e.g. a circular contour, as shown in FIG. 15.

Furthermore, also so-called Sierpinski fractals are suitable for producing interrupted thin film metallizations which exhibit an optimized resonance behavior when excited by current or voltage pulses. The Sierpinski curves shown in FIGS. 19 to 21 may be configured as shown, so that the conductive areas are defined by the dark areas. Alternatively, the pattern may also be inverted, so that the bright areas are electrically conductive. Sierpinski fractals are created, as known, according to various design provisions by repeated subdivision of a given initial shape. Although a rectangular outer contour is shown schematically in FIGS. 19 to 21, the thin film metallization 102 may have any outer contour, e.g. a circular contour, as shown in FIG. 15.

Figure 23:
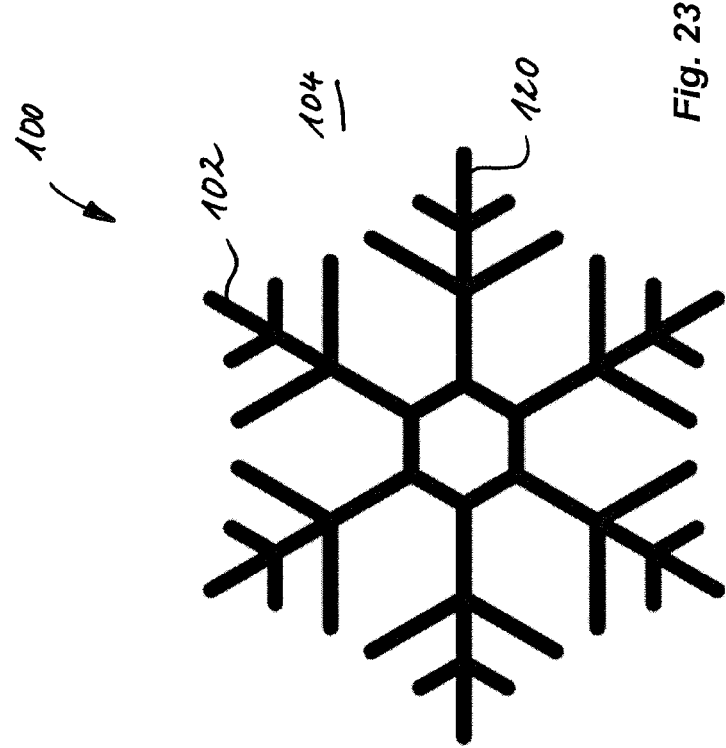
FIG. 23 is a schematic top view of an electrode arrangement according to another embodiment.
Figure 22:
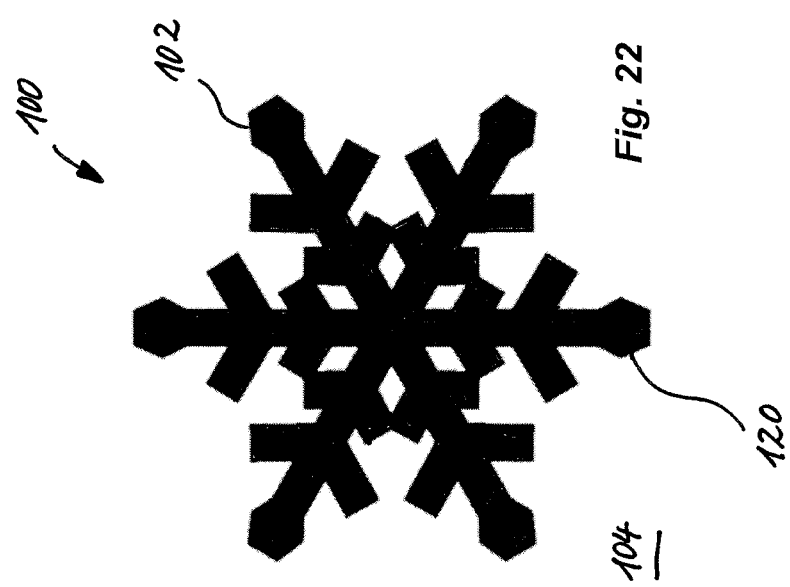
FIG. 22 is a schematic top view of an electrode arrangement according to another embodiment.

Two further possible forms of realizing such interrupted thin film metallizations 102 are shown in FIGS. 22 and 23. In both cases the electrically conductive layer of the electrode arrangement 100 has a snowflake-like geometry. FIG. 22 shows a locally varying width of the conductive paths 120, while FIG. 23 shows a substantially constant width of the paths 120.

Figure 25:
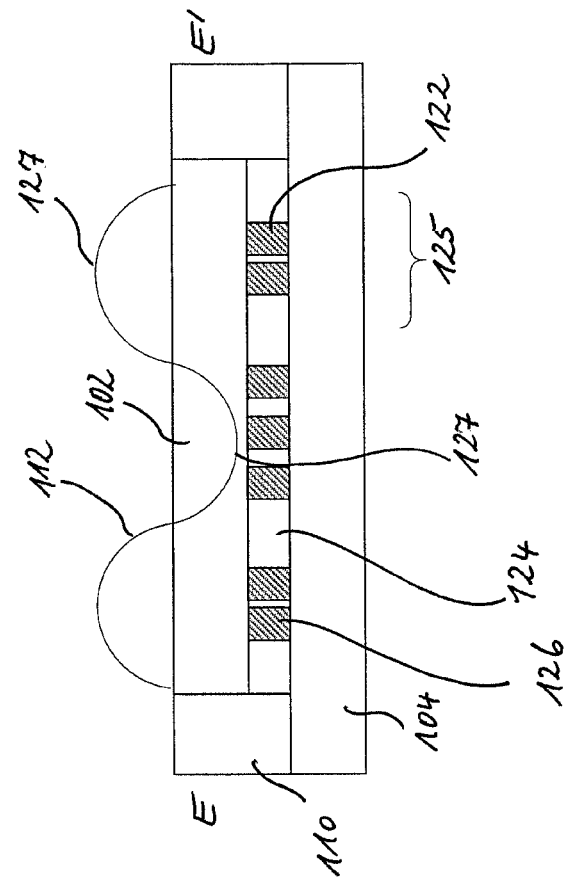
FIG. 25 is a sectional side view of FIG. 24.

Another embodiment of the present invention will be explained in more detail hereinafter with reference to FIGS. 24 and 25.

Figure 24:
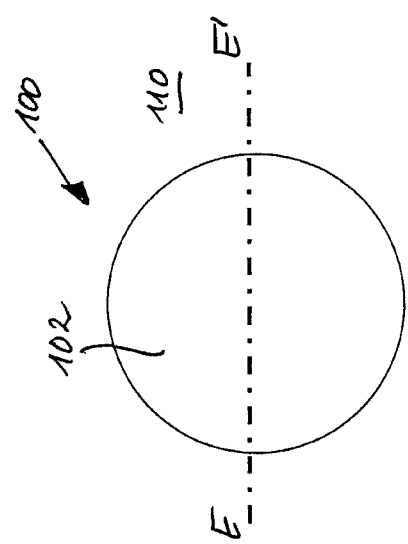
FIG. 24 is a schematic top view of an electrode arrangement according to another embodiment.

FIG. 24 shows a schematic top view of an electrode arrangement 100 with a circular closed thin film metallization, which corresponds in its dimensions to the known implantable electrodes referred to in the above articles. The electrically conductive layer 102 is embedded on a carrier structure 104 (also referred to as "substrate") in an opening of a top layer 110, as can be seen from the sectional view of FIG. 25. An adhesion promoting layer 122 is arranged between the electrically conductive layer 102 and the carrier structure 104. According to the present invention, this adhesion promoting layer 122 is not continuous but structured. The adhesion promoting layer 122 has, in particular, interruptions 124 alternating with so-called bumps 126. These interruptions 124 are filled up with the thin film metallization 102. The local fractalization includes a structuring of the adhesion promoting layer, so that the adhesion varies over the electrode area in a distributed manner This kind of fractalization of the electrode adhesion promoting layer 122 between the surface metallization 102 and the substrate 104 leads to local stiffening, e.g. in the area 125 shown in FIG. 25, and local anchoring points (referred to as bumps 126) are set between the metallization 102 and the substrate 104 as local adhesion promoters. According to the present invention, the bumps 126 are placed at the local points of mechanical oscillation maxima 127 of the thin film metallization 102. On the one hand, this allows the deflection to be reduced by local strengthening through adhesion at points where oscillation maxima 127 would otherwise occur. On the other hand, a local weakening (i.e. no adhesion) of the thin film metallization 102 is accomplished at the locations of interruptions 124 by local non-adhesion (by not setting bumps 126) at the points where oscillation minima, i.e. zero crossings of the depicted oscillation curve 112, occur in the non-modified electrode arrangement. In this way, the mechanical resonance response is reduced in a globally distributed manner over the entire electrode area.

In a further embodiment, the local fractalization exhibits, distributed over the electrode area, a variation of the thickness of the thin film layer. For example, the resonance behavior can be optimized by surface fractalization or self-similar surfaces of the thin film electrode.

Figure 27:
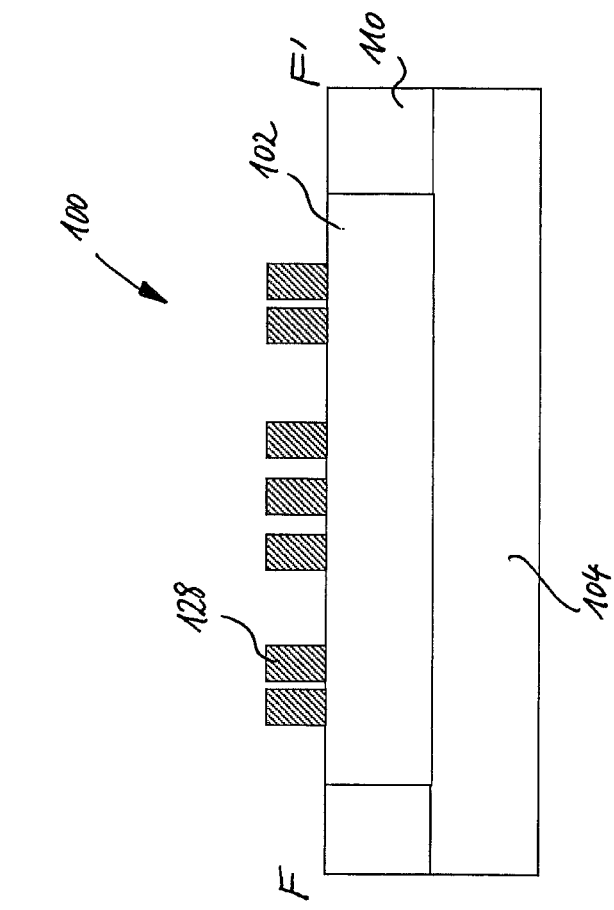
FIG. 27 is a sectional side view of FIG. 26.
Figure 26:
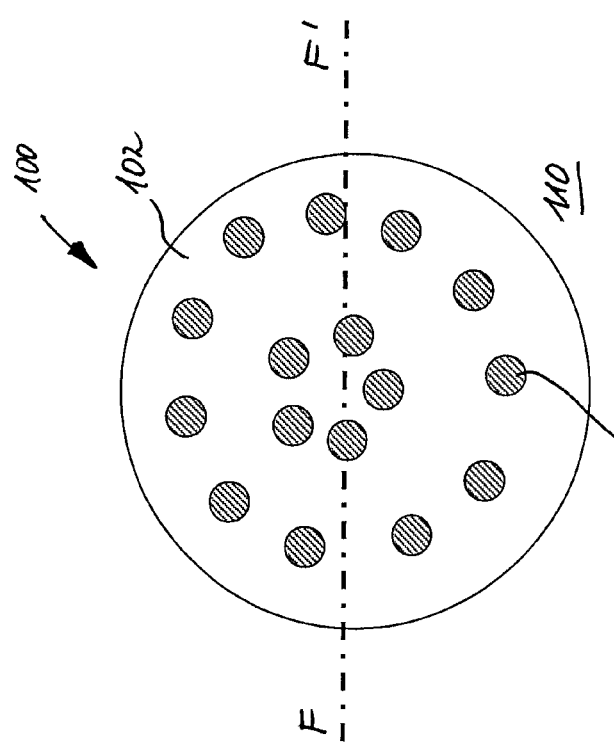
FIG. 26 is a schematic top view of an electrode arrangement according to another embodiment.

An embodiment of an electrode arrangement 100 according to the present invention will be explained in the following with reference to FIGS. 26 and 27. According to this embodiment, a circular thin film metallization 102 is applied to the carrier structure 104 and embedded in a top layer 110. The surface of the thin film metallization 102 has arranged thereon elevations 128 formed e.g. by hill structures. These elevations 128 form a fractalized three-dimensional structure of the thin film surface. The elevations 128 lead to a local strengthening of the thin film metallization 102 at the locations where oscillation maxima occur in the non-modified thin film metallization. This surface fractalization may be accomplished, for example, by 3D structuring with globally inhomogeneously distributed micro-hill structures, bumps, placed at the local points of mechanical oscillation maxima for global oscillation damping/resonance minimization. Here, it should be emphasized once more that the representation of the elevations 128 is highly schematic, since the structures are much finer in reality. Furthermore, the depicted placement of the elevations 128 is sketched only exemplarily. The elevations 128 may be produced from a great variety of materials. On the one hand, they may be part of the metallization itself. On the other hand, also polymer structures or other suitable materials may be used.

Figures 28, 29:
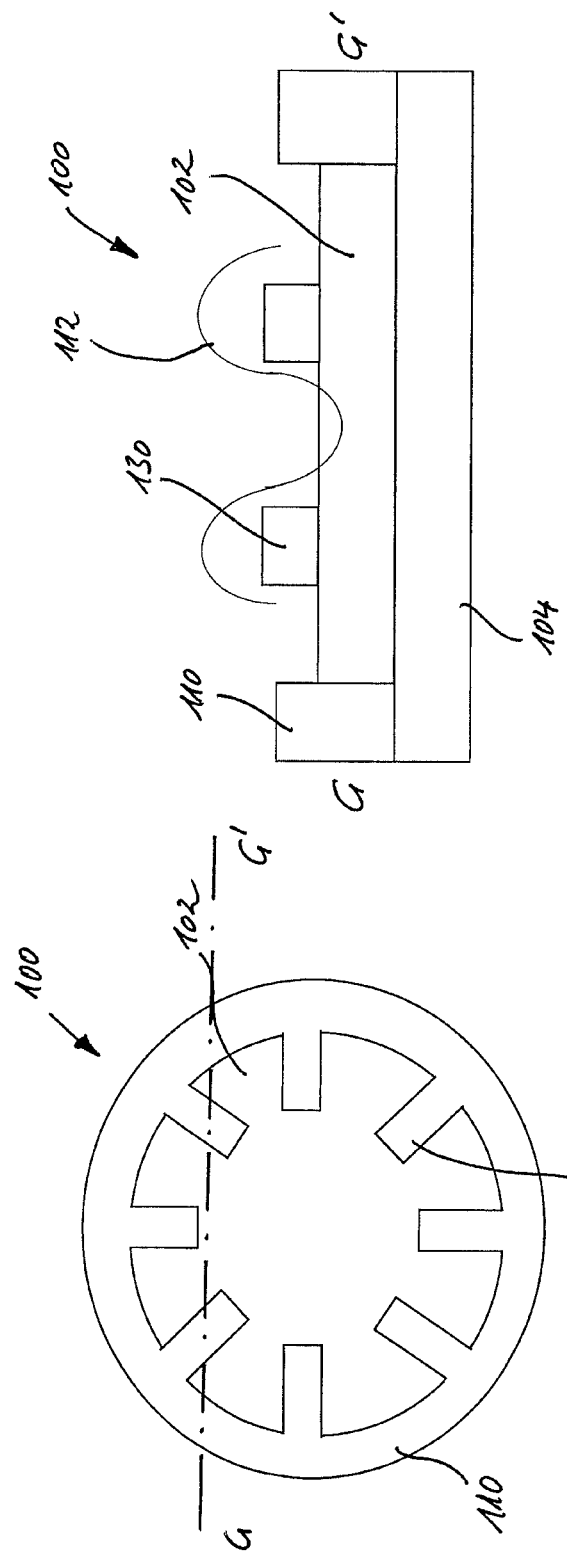
FIG. 28 is a schematic top view of an electrode arrangement according to another embodiment.
FIG. 29 is a sectional side view of FIG. 28.

Damping of the mechanical oscillations (indicated by the oscillation curve 112) can also be achieved by structured elements of the top layer 110. An example of this type of continuity interruption is shown in FIGS. 28 and 29. The thin film metallization 102 is here deposited on a carrier structure 104 and embedded in a top layer 110. According to the embodiment shown here, the top layer has finger-shaped webs 130, which extend radially towards the interior of the electrically conductive layer. In the example shown, eight webs 130 are provided, which are evenly and symmetrically distributed around the circumference. However, a person skilled in the art will, of course, be aware that arbitrary other numbers of webs 130 and also an asymmetrical distribution may be provided as well. The webs 130 may only rest on the thin film electrode 102 or firmly adhere thereto. This provides local mechanical oscillation damping through the top layer 110 from the upper side.

Figure 30:
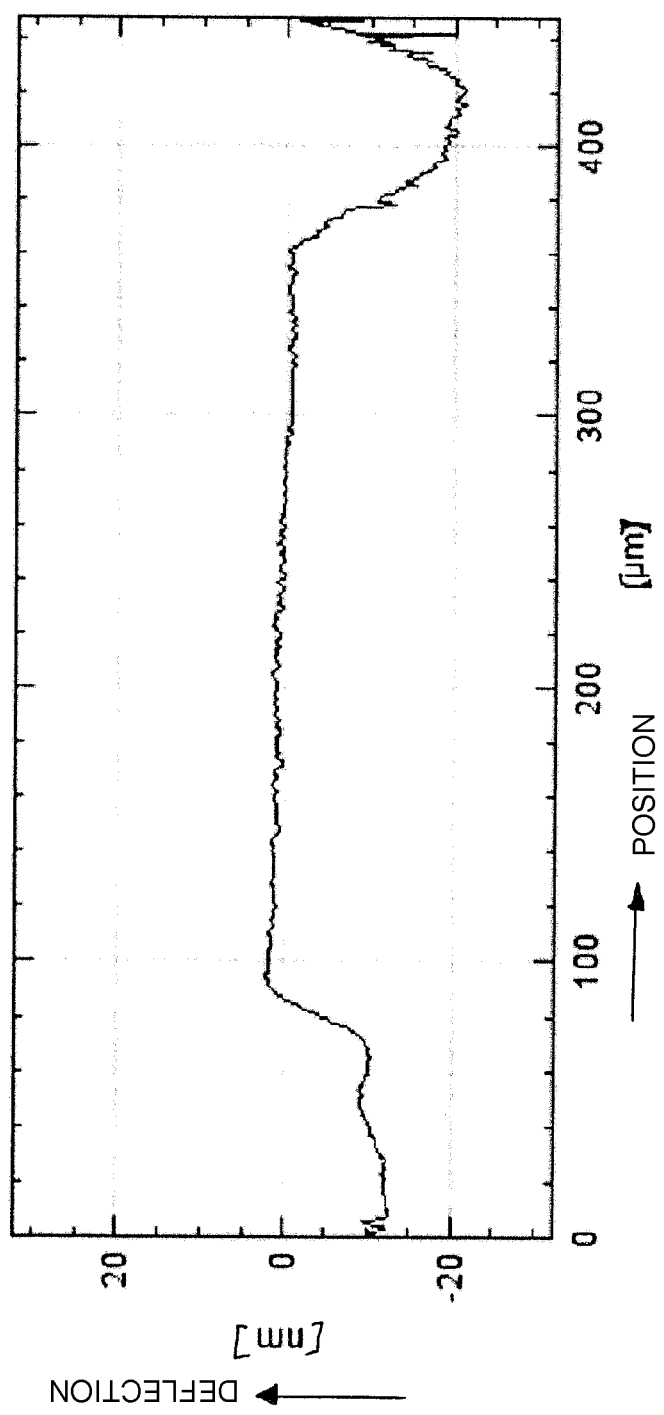
FIG. 30 is a schematic graph of a deflection of an electrode arrangement along a straight line across the electrode area in response to stimulation with a square wave signal.

When such electrode structures are designed, the resonance response of a thin film metallization 102 with the desired external dimensions is first determined for the relevant excitation signals. FIG. 30 shows exemplarily the deflection of a platinum thin-film electrode (in nanometers) over the entire electrode area along a central diameter (in micrometers), this deflection occurring, by way of example, as a mechanical response to an electrical stimulation with an excitation signal (e.g. a square wave signal) in the range from 1 Hz to 100 kHz. Then, for example, the appropriate locations for setting adhesion promoting bumps 126 and interruptions 124 or the type of one of the other modifications described above are determined. In a subsequent check it can be determined whether the desired effect has been achieved or whether further modifications of the thin film metallization will still be necessary.

Although this is not shown in the figures, local fractalization may include a variation of defect density distributed over the electrode area in the electrically conductive material of the electrode. By adapting the defect density, the intrinsic layer stress in the thin film microstructure will be adapted, so that the resonance behavior will be optimized. The defect density can be controlled e.g. by adjusting the production parameters of sputtered and vapor-deposited thin film layers, so that a resonance behavior will be minimized.

The resonance response can be determined both by actual measurement, e.g. by digital holography during electrical stimulation, and by suitable simulation methods. In an embodiment, the mechanical deflection of the thin film electrodes in response to an applied alternating electric field is recorded by digital holography in situ simultaneously during stimulation. The mechanical deformation, the oscillation amplitude and/or the spatially resolved oscillation phase as well as a possible mechanical failure of the electrode after stimulation can be recorded in top view with the aid of a normal optical light microscope.

With this investigative approach, thin film electrodes can be examined with respect to their resonance behavior in response to electrical stimulation for a great variety of applications in the field of neuroprosthetics, and adapted and designed to have a long-term mechanical stability.

In summary, the present invention provides a possibility of increasing the long-term stability of implantable electrode arrangements by compensating oscillations through the electrode design. In particular, the local thin film geometry and the local thin film area, the thin film edge area, the thin-film topography (by hill structures, bumps or "egg-carton" structures) are fractalized for a global homogeneous electric field distribution and mechanical oscillation (resonance of the electrode), or the adhesion promoting topography is fractalized by local mechanical weakening and strengthening of the thin film and substrate surface topography for local damping of the thin film at the oscillation maxima.

The thin film systems take into account the chemical and mechanical stress mechanisms, which occur in vivo during electric stimulation and which lead to plastic deformation and a loss of film integrity of the thin film, and they counteract the mechanical deformation. The resonance-adapted design of the electrodes provides an oscillation compensation adapted to the different specifications of the various fields of use of functional neural electric stimulation. This leads to an improvement of the mechanical stability and an adaptation of the design to individual stimulation patterns of the thin films and thus increases the durability of the electrodes. The thin film systems are designed for optimum mechanical voltage compensation.

The electrode arrangement according to the various embodiments described above is advantageous insofar as stress corrosion cracking, corrosion fatigue and thin film/thin film as well as thin film/substrate adhesion losses can be reduced or prevented. A homogenization of the global electric field and of the ion currents generated can be achieved. Furthermore, the oscillation characteristics can be adapted to the application-specific electric stimulation requirements in an advantageous manner. As a result, degradation mechanisms can be reduced or fully eliminated and the thin film metallization has a longer long-term stability, making it thus more suitable for implantation and chronic innervation with the nervous system. Moreover, the electrode arrangement can be manufactured on the basis of thin film technology alone.

Furthermore, it should be emphasized that a plurality of or all of the above described fractalization mechanisms may be combined with one another in an arbitrary manner, so as to achieve the desired low resonance of the electrode.

The present invention additionally relates to a method of designing an electrode arrangement, the method comprising the following steps:

providing a start configuration of a flexible implantable electrode arrangement comprising an electrically insulating carrier structure and an electrically conductive layer, which includes an electrically conductive thin film layer, the electrically conductive thin film layer being structured so as to form at least one implantable electrode;

exciting the electrode arrangement with an alternating excitation voltage or an alternating excitation current;

determining a mechanical deflection of the electrode arrangement in response to the excitation with the excitation voltage or the excitation current; and modifying the electrode arrangement so that a mechanical resonance of the electrode in response to the electric excitation with the excitation voltage or the excitation current will assume a minimum.

Modifying the electrode arrangement comprises, in an advantageous manner, a local fractalization of the electrode in one of the above-explained embodiments.

What is claimed is:

1. An implantable electrode arrangement, comprising:
an electrically insulating carrier structure; and
an electrically conductive layer including an electrically conductive thin film layer, the electrically conductive thin film layer being structured to form at least one implantable electrode, the at least one implantable electrode has a local fractalization through a self-similar structuring chosen such that a mechanical resonance of the electrode in response to electric excitation with an excitation voltage at which the electrode undergoes mechanical resonance is minimized.

2. The implantable electrode arrangement according to claim 1, wherein the local fractalization includes a structuring of a contour of the electrode.

3. The implantable electrode arrangement according to claim 2, wherein an electrode area is defined by a self-similar Mandelbrot geometry.

4. The implantable electrode arrangement according to claim 2, wherein locally different conditions between an electrode diameter and an electrode area are set.

5. The implantable electrode arrangement according to claim 4, wherein the contour has a star-shaped or a snowflake-like geometry.

6. The implantable electrode arrangement according to claim 1, wherein the local fractalization includes an interruption of the electrically conductive thin film layer.

7. The implantable electrode arrangement according to claim 6, wherein the interruption is formed by partially covering the electrically conductive thin film layer with an electrically insulating layer.

8. The implantable electrode arrangement according to claim 6, wherein the interruption is formed by embedding a plurality of electrically conductive paths into the electrically insulating carrier structure.

9. The implantable electrode arrangement according to claim 1, wherein an adhesion promoting layer is arranged between the electrically insulating carrier structure and the electrically conductive thin film layer.

10. The implantable electrode arrangement according to claim 9, wherein the local fractalization includes a structuring of the adhesion promoting layer, the adhesion promoting layer varies over an electrode area in a distributed manner.

11. The implantable electrode arrangement according to claim 1, wherein the local fractalization exhibits, distributed over an electrode area, a variation of a thickness of the electrically conductive thin film layer.

12. The implantable electrode arrangement according to claim 11, wherein an electrode surface is locally strengthened by a plurality of elevations distributed over the electrode area.

13. The implantable electrode arrangement according to claim 1, wherein the local fractalization includes, distributed over an electrode area, a variation of a defect density in the electrically conductive thin film layer.

14. The implantable electrode arrangement according to claim 1, wherein the electrically insulating carrier structure is a polymer material.

15. The implantable electrode arrangement according to claim 1, wherein the electrically conductive thin film layer is platinum, iridium and/or iridium oxide.

16. The implantable electrode arrangement according to claim 15, wherein the electrically conductive thin film layer is coated with metals, metal oxides, metal nitrides or carbon layers.

* * * * *